United States Patent
Pérez Cano et al.

(10) Patent No.: US 11,642,359 B2
(45) Date of Patent: May 9, 2023

(54) NUTRITIONAL COMPOSITION FOR IMPROVING INTESTINAL BARRIER INTEGRITY, PREPARATION OF THE COMPOSITION AND METHOD OF TREATMENT

(71) Applicant: N.V. Nutricia, Zoetermeer (NL)

(72) Inventors: Francisco José Pérez Cano, Barcelona (ES); Catharina Theresia Knipping, Utrecht (NL); Bernd Stahl, Utrecht (NL)

(73) Assignee: N.V. Nutricia

( * ) Notice: Subject to any disclaimer, the term of this patent is extended or adjusted under 35 U.S.C. 154(b) by 181 days.

(21) Appl. No.: 17/253,128

(22) PCT Filed: Jul. 12, 2018

(86) PCT No.: PCT/NL2018/050477
§ 371 (c)(1),
(2) Date: Dec. 17, 2020

(87) PCT Pub. No.: WO2020/013683
PCT Pub. Date: Jan. 16, 2020

(65) Prior Publication Data
US 2021/0252029 A1    Aug. 19, 2021

(51) Int. Cl.
| | | |
|---|---|---|
| *A61K 31/702* | (2006.01) | |
| *A23L 33/19* | (2016.01) | |
| *A23L 33/115* | (2016.01) | |
| *A23L 33/21* | (2016.01) | |
| *A23L 33/00* | (2016.01) | |
| *A61P 1/00* | (2006.01) | |
| *A23C 9/20* | (2006.01) | |
| *A61K 9/00* | (2006.01) | |
| *A61K 31/202* | (2006.01) | |

(52) U.S. Cl.
CPC .......... *A61K 31/702* (2013.01); *A23C 9/206* (2013.01); *A23L 33/115* (2016.08); *A23L 33/19* (2016.08); *A23L 33/21* (2016.08); *A23L 33/40* (2016.08); *A61K 9/0053* (2013.01); *A61K 31/202* (2013.01); *A61P 1/00* (2018.01)

(58) Field of Classification Search
None
See application file for complete search history.

(56) References Cited

U.S. PATENT DOCUMENTS

2017/0202864 A1    7/2017    Gallardo et al.

FOREIGN PATENT DOCUMENTS

| WO | 2012092155 A1 | 7/2012 |
| WO | 2019092160 A2 | 7/2012 |
| WO | 2017103850 A1 | 6/2017 |

OTHER PUBLICATIONS

Taylor, S. N., Basile, L. A., Ebeling, M., & Wagner, C. L. (2009). Intestinal permeability in preterm infants by feeding type: mother's milk versus formula. Breastfeeding medicine, 4(1), 11-15. (Year: 2009).*
Jacobi, S. K., Moeser, A. J., Blikslager, A. T., Rhoads, J. M., Corl, B. A., Harrell, R. J., & Odle, J. (2013). Acute effects of rotavirus and malnutrition on intestinal barrier function in neonatal piglets. World journal of gastroenterology: WJG, 19(31), 5094. (Year: 2013 ).*
Oliveros, E., Ramirez, M., Vazquez, E., Barranco, A., Gruart, A., Delgado-Garcia, J. M., . . . & Martin, M. J. (2016). Oral supplementation of 2'-fucosyllactose during lactation improves memory and learning in rats. The Journal of nutritional biochemistry, 31, 20-27. (Year: 2016).*
Poroyko, V., Mirzapoiazova, T., Carlisle, E. M., Caplan, M. S., Alverdy, J., Morawitz, M. J., . . . & Liu, D. (2012). Breast Milk and Formula Feeding Affect Intestinal Epithelial Barrier Function in Vivo and in Vitro. Journal of Surgical Research, 172(2), 302. (Year: 2012).*
König, J., Wells, J., Cani, P. D., Garcia-Rodenas, C. L., MacDonald, T., Mercenier, A., . . . & Brummer, R. J. (2016). Human intestinal barrier function in health and disease. Clinical and translational gastroenterology, 7(10), e196. (Year: 2016).*

* cited by examiner

*Primary Examiner* — Dale R Miller
(74) *Attorney, Agent, or Firm* — N.V. Nederlandsch Octrooibureau

(57) ABSTRACT

The invention concerns composition comprising 2'-fucosyl-lactose for use in the treatment of virus induced diarrhea.

17 Claims, 1 Drawing Sheet

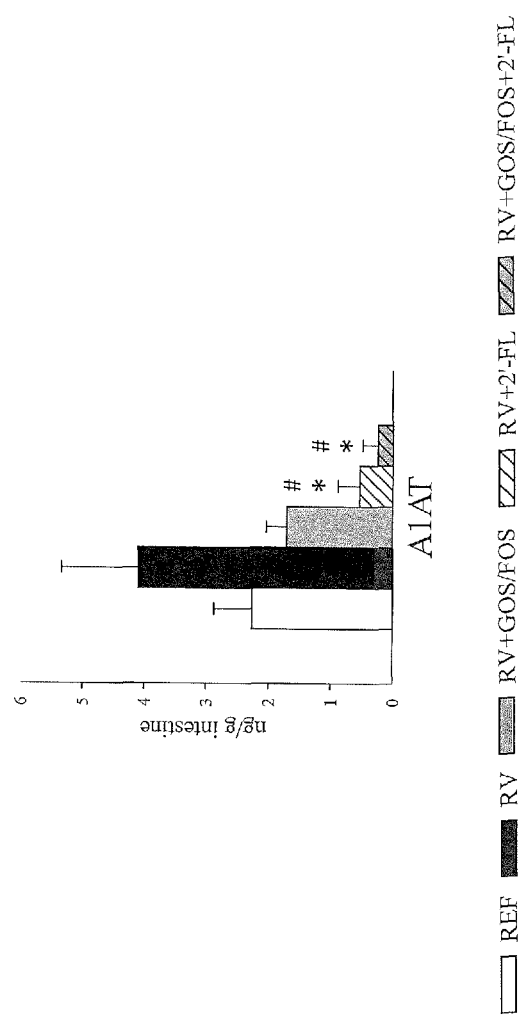

NUTRITIONAL COMPOSITION FOR IMPROVING INTESTINAL BARRIER INTEGRITY, PREPARATION OF THE COMPOSITION AND METHOD OF TREATMENT

FIELD OF THE INVENTION

The present invention relates to infant nutrition with non-digestible oligosaccharides, in particular to the use thereof for improving intestinal barrier integrity.

BACKGROUND OF THE INVENTION

Human milk is regarded as the gold standard of infant nutrition due to its unique and unrivalled combination of nutritive and functional components. Therefore, it is recommended by, amongst others, the WHO that infants be provided human milk exclusively up to 6 months of age. Unfortunately, this is not always possible and in those instances parents need to rely on infant formula that provide the best possible substitute or additional nutrition for human milk.

Especially at the start of life nutritional support is needed for maturation and protection of the infant's gastrointestinal tract. The gastrointestinal epithelium normally functions as a selective barrier permitting the absorption of nutrients, electrolytes and water and preventing the exposure to dietary and microbial antigens, including food allergens. Human milk provides several bioactive factors that benefit the relatively immature immune system of neonates early in life. These components have been categorized into two different groups according to either their protective role or their ability to promote maturation. In this sense, human milk oligosaccharides (HMOS) are considered to play a part both in protection and maturation. In the search for infant formulae with an optimal composition in order to mimic the beneficial effects of human milk as close as possible, quite some attention has been given to human milk oligosaccharides.

The 162 structures of HMOS discovered to date and described in Urashima et al. (Trends in Glycoscience and Glycotechnolology, 2018, 30; 172, SE51-SE65) exhibit a lactose, polylactosamine or lacto-N-biose core, which can be further bound to either fucose or sialic acids or both. This structure confers on them a high chemical variability and protection from digestion. Therefore, the majority of HMOS are neither absorbed nor metabolized in the proximal gut and reach the distal gut undigested to exert prebiotic effects on certain bacterial populations, to reinforce the intestinal barrier and to protect against enteropathogen infections. HMOS are present in human breast milk in a relatively high proportion (5-20 g/L). The most abundant HMOS is 2'-fucosyllactose (2'-FL), representing ~20% of the total oligosaccharides in human breast milk. In vitro and in vivo studies with 2'-FL have evidenced its immunomodulatory effects, which include promoting anti-inflammatory activities (He et al. Gut 2016; 65:33-46 and the inhibition of the colonization of pathogens (Ruiz-Palacios et al. J Biol Chem 2003; 278:14112-20.

Holscher et al., J Nutr 2014; 144:586-591 studied the influence of HMOS on maturation of certain human intestinal cell lines. To 2'-fucosyllactose, a role as promotor of intestinal cell proliferation was ascribed. A modest enhancement of transepithelial resistance, which can be taken as an indicator of barrier integrity, was ascribed to lacto N—N-neotetraose (LNnT).

Documents like WO 2012/092155, WO 2013/032674, WO 2016/066175 and WO 2012/092160 all describe human milk oligosaccharides, including 2'-fucosyllactose and mention barrier function, but none of them establishes an enabling link between for 2'-fucosyllactose on barrier function, in particular no effect of 2'-fucosyllactose has been shown in the art on barrier permeability and intestinal epithelial cell disruption.

SUMMARY OF THE INVENTION

Alpha-1 antitrypsin (A1AT) is a protease inhibitor and is resistant to degradation by digestive enzymes. It is an endogenous marker for the presence of blood proteins in the intestinal tract. The inventors found that in a neonatal rat model upon infection with rotavirus, intestinal barrier function was disrupted as evidenced by high levels alpha-1 antitrypsin (A1AT) in the gut wash and that a remarkable counteraction of this disrupted barrier function could be achieved by the presence of 2'-fucosyllactose. Just as surprisingly, the inventors found that this improvement of intestinal barrier function was not only achieved under the circumstance that intestinal barrier function was impaired, but the intestinal barrier function was actually also improved compared to the control group as evidence by a significant reduction of A1AT in the gut wash compared to the control group.

Moreover, the inventors found that in the circumstance of rotavirus induced disruption of intestinal barrier function as well as compared to the non-infected control group, the additional presence of non-digestible oligosaccharide resulted in that the intestinal barrier function was even further improved.

DETAILED DESCRIPTION OF THE INVENTION

The present invention thus concerns a method for the treatment of virus induced intestinal barrier disruption in a human subject by administering a nutritional composition that comprises a fucosylated human milk oligosaccharide (HMO), preferably 2'-fucosyllactose.

In other words, the invention concerns a nutritional composition comprising a fucosylated human milk oligosaccharide (HMO), preferably 2'-fucosyllactose, for use in the treatment of virus induced intestinal barrier disruption in a human subject.

For some jurisdictions, the invention can also be worded as the use of a fucosylated human milk oligosaccharide (HMO), preferably 2'-fucosyllactose, for the preparation of a nutritional composition for the treatment of virus induced intestinal barrier disruption in a human subject.

The present invention also concerns a method for improving intestinal barrier integrity in a human subject by administering a nutritional composition that comprises a fucosylated human milk oligosaccharide (HMO), preferably 2'-fucosyllactose.

In other words, the invention concerns a nutritional composition comprising a fucosylated human milk oligosaccharide (HMO), preferably 2'-fucosyllactose, for use in improving intestinal barrier integrity in a human subject.

For some jurisdictions, the invention can also be worded as the use of a fucosylated human milk oligosaccharide (HMO), preferably 2'-fucosyllactose, for the preparation of a nutritional composition for improving intestinal barrier integrity in a human subject.

The amount of the fucosylated HMO, preferably 2'-fucosyllactose, is preferably an effective amount for the treatment of virus induced intestinal barrier disruption in a human subject and/or an effective amount for improving intestinal barrier integrity.

Fucosylated Human Milk Oligosaccharides and 2'-Fucosyllactose

Prebiotics are typically indigestible sugar-type compounds such as non-digestible oligosaccharides (NDOs). These compounds pass through the first part of the gastro-intestinal tract substantially without being digested. In the intestine these compounds are fermented by the microbiota releasing, amongst others, short chain fatty acids which are adsorbed by the human body.

There are many sources of NDO's, amongst which is human breast milk. Usually these oligosaccharides are denoted as human milk oligosaccharides (HMOS). Typical NDOs used in infant foods are GOS and FOS.

Human milk is the preferred food for infants and is also denoted as the golden standards. Human milk contains a particularly high level of oligosaccharides of roughly 10 to 15 g/L, which is typically much more than the level of NDO in the milk from domestic animals. Also, compared to the NDOs in the milk of domestic animals, HMOS are structurally different. Human NDO is very complex and consists of a heterogenic group of many different compounds with diverse sugar composition. Because of their complex and polymorphic structure, large-scale synthesis is complicated. It is therefore not yet technically and economically feasible to prepare compositions, such as infant formulas, with NDO composition identical to human milk. In the method or use according to the present invention, a fucosylated non-digestible human milk oligosaccharide is used.

Fucosyllactose (FL) is a fucosylated non-digestible oligosaccharide present in human milk. It is not present in bovine milk. It consists of three monose units, fucose, galactose and glucose linked together. Lactose is a galactose unit linked to a glucose unit via a beta 1,4 linkage. A fucose unit is linked to a galactose unit of a lactose molecule via an alpha 1,2 linkage (2'-fucosyllactose, 2'-FL) or via an alpha 1,3 linkage to the glucose unit of a lactose (3-Fucosyllactose, 3-FL). 2'FL is the most abundant NDO in human milk. The HMOS used in the current invention is 2'-FL. In particular administration of 2'-FL resulted in an improvement of intestinal barrier integrity and also administration of 2'-FL resulted in a curative effect on virus induced intestinal barrier disruption.

2'-FL, (β-L-Fuc-(1→2)-β-D-Gal-(1-4)-D-Glc) is commercially available for instance from Sigma-Aldrich. Alternatively, it can be isolated from human milk, for example as described in Andersson & Donald, 1981, J Chromatogr. 211:170-1744, or produced by genetically modified microorganisms, for example as described in Albermann et al, 2001, Carbohydrate Res. 334:97-103.

Preferably, a composition according to the invention comprises 1 mg to 3 g 2'-FL per 100 ml, more preferably 10 mg to 2 g, even more preferably 20 mg to 100 mg 2'-FL per 100 ml. Based on dry weight, the present composition preferably comprises 0.007 wt. % to 20 wt. % 2'-FL, more preferably 0.07 wt. % to 10 wt. %, even more preferably 0.15 wt. % to 1 wt. %. A lower amount of fucosyllactose will be less effective in ameliorating virus induced diarrhea, whereas a too high amount will result in unnecessary high costs of the product.

In one embodiment, the nutritional composition for use according to the present invention does not comprise lacto-N-neotetraose (LNnT). In one embodiment, the nutritional composition for use according to the present invention does not comprise a human milk oligosaccharide other than 2'-FL.

Non-Digestible Oligosaccharides Other than Human Milk Oligosaccharides

The nutritional composition preferably also comprises non-digestible oligosaccharides other than HMOS. According to the present invention, the additional presence of non-digestible oligosaccharides other than HMOS resulted in a further improvement of intestinal barrier integrity and also the additional presence of non-digestible oligosaccharides other than HMOS resulted in an improvement of the curative effect on virus induced intestinal barrier disruption.

The NDO are preferably not or only partially digested in the intestine by the action of acids or digestive enzymes present in the human upper digestive tract, in particular in the small intestine and stomach, and are fermented by the human intestinal microbiota. For example, sucrose, lactose, maltose and the common maltodextrins are considered digestible.

Preferably the present composition comprises non-digestible oligosaccharides with a DP in the range of 2 to 250, more preferably 2 to 60. The non-digestible oligosaccharide is preferably at least one, more preferably at least two selected from the group consisting of fructo-oligosaccharides, galacto-oligosaccharides, xylo-oligosaccharides, arabino-oligosaccharides, arabinogalacto-oligosaccharides, gluco-oligosaccharides, chito-oligosaccharides, glucomanno-oligosaccharides, galactomanno-oligosaccharides and mannan-oligosaccharides and furthermore milk oligosaccharides from dairy and non-dairy mammalian species. The group of fructo-oligosaccharides includes inulins and the group of galacto-oligosaccharides includes transgalacto-oligosaccharides or beta-galacto-oligosaccharides.

More preferably the present composition comprises fructo-oligosaccharides (FOS) and/or galacto-oligosaccharides (GOS), preferably the galacto-oligosaccharides comprise beta-galacto-oligosaccharides and/or alpha galactooligosaccharides. More preferably the fructo-oligosaccharides are long chain fructo-oligosaccharides (lcFOS). More preferably the galacto-oligosaccharides are short chain galacto-oligosaccharides and the beta-galacto-oligosaccharides are short chain beta-galacto-oligosaccharides. Most preferably the composition comprises long chain fructo oligosaccharides and short chain galacto-oligosaccharides. The weight ratio of short chain galacto-oligosaccharides and long chain fructo oligosaccharides lies preferably between 100:1 and 1:10, preferably between 20:1 and 1:1, preferably is about 9:1.

The galacto-oligosaccharides preferably are beta-galacto-oligosaccharides. In a particularly preferred embodiment the present composition comprises beta-galacto-oligosaccharides ([galactose]n-glucose; wherein n is an integer ranging from 2 to 60, i.e. 2, 3, 4, 5, 6, . . . , 59, 60; preferably n is selected from 2, 3, 4, 5, 6, 7, 8, 9, and 10), wherein the galactose units are in majority linked together via a beta linkage. Beta-galacto-oligosaccharides are also referred to as trans-galacto-oligosaccharides (TOS). Beta-galacto-oligosaccharides are for example sold under the trademark Vivinal™ (Borculo Domo Ingredients, Netherlands). Another suitable source is Bi2Munno (Classado). Preferably the galacto-oligosaccharides comprise beta-1,3, beta-1,4 and/or beta-1,6 linkages. In a preferred embodiment, galacto-oligosaccharides comprise at least 80% beta-1,4 and beta-1,6 linkages based on total linkages, more preferably at least 90%. In another preferred embodiment, the galactooligosaccharides comprise at least 50% beta-1,3 linkages based on total linkages, more preferably at least 60% based on total linkages.

Fructo-oligosaccharide is a NDO comprising a chain of beta-linked fructose units with a DP or average DP of 2 to 250, more preferably 2 to 100, even more preferably 10 to 60. Fructo-oligosaccharide includes inulin, levan and/or a mixed type of polyfructan. An especially preferred fructo-oligosaccharide is inulin. Fructo-oligosaccharide suitable for use in the compositions is also commercially available, e.g. Raftiline® HP (Orafti). Preferably the fructo-oligosaccharide has an average DP above 20.

In a preferred embodiment the composition comprises a mixture of inulin and short chain fructo-oligosaccharides. In a preferred embodiment the composition comprises a mixture of galacto-oligosaccharides and fructo-oligosaccharides selected from the group consisting of short chain fructo-oligosaccharides and inulin, more preferably inulin. Preferably the weight ratio in a mixture of the two different non-digestible oligosaccharides, preferably galacto-oligosaccharides and fructo-oligosaccharide, is between 25 and 0.05, more preferably between 20 and 1. Galacto-oligosaccharides, preferably beta-galacto-oligosaccharides, are more capable of stimulating bifidobacteria. Preferably the present composition comprises galacto-oligosaccharides, preferably beta-galacto-oligosaccharides, with a degree of polymerization (DP) of 2 to 10 and/or fructo-oligosaccharides with a DP of 2 to 60.

In a preferred embodiment, the composition comprises a combination of a fucosylated human milk oligosaccharide, preferably 2'-fucosyllactose, short chain galacto-oligosaccharides and long chain fructo oligosaccharides. In a preferred embodiment, the weight ratio of the sum of short chain galacto-oligosaccharides and long chain fructo oligosaccharides to 2'-fucosyllactose contained in the nutritional composition lies between 20:1 and 1:100, preferably between 10:1 and 1:50, more preferably between 4:1 and 1:20, most preferably between 1:1 and 1:15.

LC-PUFA

The composition may further comprise long chain polyunsaturated fatty acids (LC-PUFA). LC-PUFA are fatty acids wherein the acyl chain has a length of 20 to 24 carbon atoms (preferably 20 or 22 carbon atoms) and wherein the acyl chain comprises at least two unsaturated bonds between said carbon atoms in the acyl chain. More preferably the present composition comprises at least one LC-PUFA selected from the group consisting of eicosapentaenoic acid (EPA, 20:5 n3), docosahexaenoic acid (DHA, 22:6 n3), arachidonic acid (ARA, 20:4 n6) and docosapentaenoic acid (DPA, 22:5 n3), preferably DHA, EPA and/or ARA. Such LC-PUFAs have a further beneficial effect on improving intestinal barrier integrity.

The preferred content of LC-PUFA in the present composition does not exceed 15 wt. % of total fatty acids, preferably does not exceed 10 wt. %, even more preferably does not exceed 5 wt. %. Preferably the present composition comprises at least 0.2 wt. %, preferably at least 0.25 wt. %, more preferably at least 0.35 wt. %, even more preferably at least 0.5 wt. % LC-PUFA of total fatty acids, more preferably DHA. The present composition preferably comprises ARA and DHA, wherein the weight ratio ARA/DHA preferably is above 0.25, preferably above 0.5, more preferably 0.75-2, even more preferably 0.75-1.25. The weight ratio is preferably below 20, preferably between 0.5 and 5. The amount of DHA is preferably above 0.2 wt. %, more preferably above 0.3 wt. %, more preferably at least 0.35 wt. %, even more preferably 0.35-0.6 wt. % on total fatty acids.

Compositions

The present invention advantageously concerns a composition for the indicated use wherein the lipid provides 5 to 50% of the total calories, the protein provides 5 to 50% of the total calories, and the carbohydrate provides 15 to 90% of the total calories. Preferably, in the present composition the lipid provides 35 to 50% of the total calories, the protein provides 7.5 to 12.5% of the total calories, and the carbohydrate provides 40 to 55% of the total calories. For calculation of the % of total calories for the protein component, the total of energy provided by the proteins, peptides and amino acids needs to be taken into account.

The present composition preferably comprises at least one lipid selected from the group consisting of animal lipid (excluding human lipids) and vegetable lipids. Preferably the present composition comprises a combination of vegetable lipids and at least one oil selected from the group consisting of fish oil, animal oil, algae oil, fungal oil, and bacterial oil. The present composition comprising 2'-FL is not human milk.

The present composition preferably comprises protein. The protein component used in the nutritional preparation are preferably selected from the group consisting of non-human animal proteins (preferably milk proteins, preferably proteins from cow's milk), vegetable proteins (preferably soy protein and/or rice protein), free amino acids and mixtures thereof. The present composition preferably contains casein, whey, hydrolysed casein and/or hydrolysed whey protein. Preferably the protein comprises intact proteins, more preferably intact bovine whey proteins and/or intact bovine casein proteins.

The present composition preferably comprises digestible carbohydrates. The present composition preferably comprises a digestible carbohydrate component, wherein at least 35 wt. %, more preferably at least 50 wt. %, more preferably at least 75 wt. %, even more preferably at least 90 wt. %, most preferably at least 95 wt. % is lactose. The present composition preferably comprises at least 25 grams lactose per 100 gram dry weight of the present composition, preferably at least 40 grams lactose/100 gram.

When in liquid for, the nutritional composition preferably has a caloric density between 0.1 and 2.5 kcal/ml, even more preferably a caloric density of between 0.5 and 1.5 kcal/ml, most preferably between 0.6 and 0.8 kcal/ml. The amount of nutritional composition administered per day is preferably between 50 and 2000 ml, more preferably between 200 and 1500, most preferably between 400 and 1000 ml.

In one embodiment the present invention concerns a supplement, suitable to fortify human milk, to fortify human milk fortified with a standard human milk fortifier or to fortify a standard preterm formula. In the context of this invention, a supplement does not comprise all macro- and micronutrients needed for preterm infants so as to achieve a growth similar to fetal growth coupled with satisfactory functional development. The term "preterm" herein is synonymous for prematurely born and means any human infant born before the $37^{th}$ week of gestation.

Thus in one embodiment the nutritional composition according to the present invention or for use according to the present invention comprises protein, fat and/or digestible carbohydrates and is selected from the group consisting of an infant starter formula, an infant follow on formula, a toddler milk, a preterm formula, a post discharge formula and a human milk fortifier.

Application

According to the present invention, virus induced intestinal barrier disruption is treated by administering a nutritional composition comprising a fucosylated human milk oligosaccharide, preferably 2'-fucosyllactose. In a preferred embodiment, the intestinal barrier disruption that is treated is induced by rotavirus, also referred to as rotavirus induced intestinal barrier disruption. Upon intestinal infection by virus, predominantly intestinal epithelial cells are infected and disrupted. In one embodiment of the present invention, virus induced intestinal barrier disruption refers to virus induced disruption of intestinal epithelial cells.

Also according to the present invention, intestinal barrier integrity is improved by administering a nutritional composition comprising fucosylated human milk oligosaccharide, preferably 2'-fucosyllactose. The detection of A1AT in the gut wash is a measure for the permeability of the intestinal barrier. In a preferred embodiment, the improvement of intestinal barrier integrity is a reduction in the permeability of the intestinal barrier. Also in a preferred embodiment, the improvement of intestinal barrier integrity refers to a reduction of the translocation of blood components from blood to the intestinal lumen. In a preferred embodiment, the blood components are proteins. In a preferred embodiment, the improvement of intestinal barrier integrity refers to a reduction of the translocation of protein from blood to the intestinal lumen. In the context of the present invention, translocation of protein from blood to the intestinal lumen may also be referred to as protein trafficking or protein extravasation.

The nutritional composition for use according to the present invention is for use in a human subject. Preferably the human subject is an infant or a toddler. An infant is a human subject with an age form 0-12 months. A toddler is a human subject with an age form 12-36 months. In a preferred embodiment, the human subject is a preterm or prematurely born infant. Especially this subgroup of infants may benefit from being administered the fucosylated human milk oligosaccharide, preferably 2'-fucosyllactose, or a combination of the fucosylated human milk oligosaccharide, preferably 2'-fucosyllactose, and long chain fructo oligosaccharides and short chain galacto-oligosaccharides since organs making up the intestinal tract of preterms are immature, as opposed to term-born infants and thus in need of improved intestinal barrier integrity, reduced permeability of the intestinal barrier and/or reduced intestinal barrier disruption.

Preferably, the human subject is administered the fucosylated human milk oligosaccharide, preferably 2'-fucosyllactose, or the nutritional composition comprising the fucosylated human milk oligosaccharide, preferably 2'-fucosyllactose, on a daily basis. Also, the administration of the nutritional composition comprising the fucosylated human milk oligosaccharide, preferably 2'-fucosyllactose, or the use thereof, preferably commences prior to the virus induced diarrhea occurs and spans the time period the subject can be diagnosed with diarrhea.

In a preferred embodiment, the human subject is vaginally-born, also known as naturally born.

The present composition is preferably enterally administered, more preferably orally. The present composition is preferably a nutritional formula, preferably an infant formula. The present composition can advantageously be applied as a complete nutrition for infants. The present composition preferably comprises lipid, protein, and carbohydrate and is preferably administered in liquid form. The present invention includes dry compositions, e.g. powders, which are accompanied with instructions as to admix said dry compositions, in particular nutritional formula, with a suitable liquid, e.g. water.

DESCRIPTION OF THE FIGURE

The FIGURE shows the alpha-1 antitrypsin (A1AT) concentration in the gut wash was analyzed by ELISA as a measure of the intestinal barrier disruption; results are expressed as mean±S.E.M. (n=4-8); * $p<0.05$ compared to REF group; #$p<0.05$ compared to RV group (by MWU test).

EXAMPLES

Example 1

Newborn rats were distributed into five groups of 24 animals each: the reference (REF) group, rotavirus-infected (RV) group, and 3 rotavirus-infected groups supplemented with: a) a mixture of scGOS and lcFOS (RV+GOS/FOS group); b) 2'-FL (RV+2'-FL group); and c) both scGOS/lcFOS and 2'-FL (RV+GOS/FOS+2'-FL group).

Suckling rats were orally administered once daily with the same normalized volume/body weight of all products (4.5 μL/g/day), from the second to the sixteenth day of life, corresponding to the strict lactation period. The RV+GOS/FOS group was supplemented with 0.8 g of scGOS/lcFOS/100 g of body weight. The RV+2'-FL group was supplemented with 0.2 g of 2'-FL/100 g of body weight. The RV+GOS/FOS+2'-FL group received both products at the same doses as when given separately and maintaining the volume of administration (4.5 μL/g/day). The REF and RV groups were administered with a matched volume of water.

The RV (simian SA-11) was obtained as previously described (Perez-Cano et al. Pediatr Res 2007; 62:658-63), and inoculated at day 5 of life ($4 \times 10^8$ Tissue Culture Infectious Dose 50 [TCID50]/rat) in all the experimental groups with the exception of the REF group, which received the same volume of phosphate-buffered solution (PBS) under the same conditions.

Body weight was recorded daily throughout the study to assess weight gain. Half (n=12) of each group of animals were sacrificed at day 8, to analyze variables associated with the peak of diarrhea, and the other half (n=12 per group) at day 16, to analyze the effects of the supplementations once the diarrhea was resolved. Moreover, the naso-anal and tail lengths were measured to determine the body/tail ratio, the body mass index (BMI), calculated as body weight/length$^2$ (g/cm$^2$) and the Lee Index, calculated as (weight$^{0.33}$/length)×1000 (g$^{0.33}$/cm).

Sample Collection and Processing

At days 8 and 16, the half of each litter were intramuscularly anesthetized with ketamine (90 mg/kg) (Merial Laboratories S.A., Barcelona, Spain) and xylazine (10 mg/kg) (Bayer A.G., Leverkusen, Germany), exsanguinated and their intestines were obtained. The intestines were opened lengthwise, cut into 5 mm pieces and incubated with 2 mL of PBS in a shaker (10 min, 37° C.) to obtain the gut wash (GW). After centrifugation, supernatants were stored at −20° C. and −80° C. until alpha-1 antitrypsin (A1AT) analysis.

The quantification of A1AT in the gut wash, as a marker of intestinal permeability, was performed with the rat SERPINA1/Alpha 1 Antitrypsin ELISA kit (LifeSpan Biosciences Inc., Seattle, Wash., USA) following the manufacturer's instructions. The standard concentrations ranged from 100 to 1.563 ng/mL. Assay sensitivity was 1.56 ng/mL.

Statistical Analysis

The Statistical Package for the Social Sciences (SPSS v22.0) (IBM, Chicago, Ill., USA) was used for statistical analysis. Data was tested for homogeneity of variance and normality distribution by the Levene's and Shapiro-Wilk tests, respectively. When data was homogeneous and had a normal behavior, conventional one-way ANOVA test followed by the post hoc Bonferroni was performed. Otherwise, the nonparametric Kruskal-Wallis test followed by the post hoc Mann-Whitney U (MWU) test were performed. Finally, the chi-square test was used to compare frequencies of diarrhea incidence. Significant differences were established when p<0.05.

Results

Growth

The RV infection did not produce any significant change in growth either at the peak of diarrhea (day 8) or at the end of the study (day 16), as shown by the results in body weight, body/tail ratio, BMI and Lee Index (Table 1). The group supplemented with scGOS/lcFOS had a slightly higher body weight at the end of the study (day 16, p<0.05), and although none of these growth changes modified the BMI, some differences were seen in the body/tail length ratio and the Lee Index. All supplementations increased the body/tail length ratio compared to REF or RV at some time point. Moreover, the Lee Index was decreased exclusively at the peak of diarrhea compared to REF.

reduced extravasation of A1AT protein and its trafficking towards the gut lumen. The treatment of intestinal barrier disruption was studied on the $3^{rd}$ day of the diarrheal period which corresponds to the observed peak in the severity of diarrhea in the studied animals.

Example 2: Infant Formula for the Treatment of Virus Induced Intestinal Barrier Disruption An infant formula according to the invention comprising per 100 ml (13.9 dry weight):
 1.4 g protein (whey and casein)
 7.3 g digestible carbohydrates (including lactose)
 3.6 g fat (vegetable fat, fish oil)
 0.6 g non-digestible oligosaccharides of which 60 mg 2'-fucosyllactose and 480 mg beta-galacto-oligosaccharides, and 60 mg fructo-oligosaccharides
Further are included: choline, myo-inositol, taurine, minerals, trace elements, and vitamins in accordance with guidelines.

The invention claimed is:

1. A method for the treatment of rotavirus induced intestinal barrier disruption in an infant or toddler by adminis-

TABLE 1

Growth-associated variables

|  | REF | RV | RV + GOS/FOS | RV + 2'-FL | RV + GOS/FOS + 2'-FL |
|---|---|---|---|---|---|
| Body weight (g) | | | | | |
| day 8 | 13.52 ± 0.25 | 13.60 ± 0.19 | 14.08 ± 0.17 | 13.51 ± 0.19 | 13.67 ± 0.19 |
| day 16 | 31.40 ± 0.89 | 31.91 ± 0.65 | 34.16 ± 0.55*# | 32.79 ± 0.50 | 33.53 ± 0.40 |
| Body/tail length ratio | | | | | |
| day 8 | 2.14 ± 0.07 | 2.15 ± 0.03 | 2.26 ± 0.03*# | 2.32 ± 0.03*# | 2.22 ± 0.03 |
| day 16 | 1.77 ± 0.02 | 1.77 ± 0.02 | 1.92 ± 0.04*# | 1.86 ± 0.05 | 1.84 ± 0.03* |
| BMI (g/cm$^2$) | | | | | |
| day 8 | 0.30 ± 0.01 | 0.29 ± 0.00 | 0.29 ± 0.00 | 0.28 ± 0.01 | 0.28 ± 0.00 |
| day 16 | 0.35 ± 0.01 | 0.36 ± 0.00 | 0.37 ± 0.01 | 0.37 ± 0.01 | 0.36 ± 0.00 |
| Lee Index | | | | | |
| day 8 | 354.76 ± 3.42 | 348.80 ± 1.73 | 345.21 ± 1.34* | 343.49 ± 2.46*# | 344.52 ± 1.43* |
| day 16 | 334.44 ± 2.51 | 335.88 ± 2.41 | 337.12 ± 3.36 | 337.93 ± 3.48 | 332.44 ± 1.26 |

Results are expressed as mean ± S.E.M. (n = 12); *p < 0.05 compared to REF (by MWU test); #p < 0.05 compared to RV (by MWU test).

Intestinal Barrier Function

Alpha-1 antitrypsin (A1AT) belongs to the serpin superfamily and is known as a protease inhibitor. It is resistant to degradation by digestive enzymes and is an endogenous marker for the presence of blood proteins in the intestinal tract.

The A1AT levels in the gut wash (see FIGURE) were determined by ELISA to assess the changes in the gut permeability. The serum level of A1AT is significantly elevated during the inflammatory response and can be transported across the intestinal epithelial layer into the intestinal lumen due to the increased permeability of the intestinal epithelial barrier (Yang et al. Sci Rep 2015; 5: 15004). The RV group displayed higher levels of A1AT in the gut wash, but they did not differ statistically from the REF group. However, the supplementation with 2'-FL and GOS/FOS+2'-FL reduced the concentration of A1AT in the gut wash compared to both the RV and REF (p<0.05), indicating that not only were they able to treat the gut permeability disruption induced by RV, but they also promoted an enhanced gut barrier function evidenced by the tering a nutritional composition that comprises 2'-fucosyllactose, wherein the nutritional composition is selected from an infant formula and a follow-on and which is not human milk.

2. The method according to claim 1, wherein the virus induced intestinal barrier disruption is virus induced disruption of intestinal epithelial cells.

3. The method according to claim 1, wherein the nutritional composition further comprises at least one non-digestible oligosaccharides with a DP in the range of 2 to 250, wherein the non-digestible oligosaccharides are selected from the group consisting of fructo-oligosaccharides, galacto-oligosaccharides, xylo-oligosaccharides, arabino-oligosaccharides, arabinogalacto-oligosaccharides, gluco-oligosaccharides, chito-oligosaccharides, glucomanno-oligosaccharides, galactomanno-oligosaccharides and mannan-oligosaccharides.

4. The method according to claim 3, wherein the non-digestible oligosaccharides are selected from the group consisting of fructo-oligosaccharides and galacto-oligosaccharides.

5. The method according to claim 1, wherein the nutritional composition further comprises at least one long chain polyunsaturated fatty acids (LC-PUFA) selected from the group consisting of eicosapentaenoic acid (EPA, 20:5 n3), docosahexaenoic acid (DHA, 22:6 n3), arachidonic acid (ARA, 20:4 n6) and docosapentaenoic acid (DPA, 22:5 n3).

6. The method according to claim 1, wherein the human subject is an infant.

7. The method according to claim 1, wherein the nutritional composition is an infant formula.

8. The method according to claim 1, wherein the nutritional composition further comprises at least two non-digestible oligosaccharides with a DP in the range of 2 to 250, wherein the non-digestible oligosaccharides are selected from the group consisting of fructo-oligosaccharides, galacto-oligosaccharides, xylo-oligosaccharides, arabino-oligosaccharides, arabinogalacto-oligosaccharides, gluco-oligosaccharides, chito-oligosaccharides, glucomanno-oligosaccharides, galactomanno-oligosaccharides and mannan-oligosaccharides.

9. The method according to claim 8, wherein the nutritional composition further comprises fructo-oligosaccharides and galacto-oligosaccharides.

10. The method according to claim 1, wherein the nutritional composition further comprises at least one long chain polyunsaturated fatty acids (LC-PUFA) selected from the group consisting of docosahexaenoic acid (DHA, 22:6 n3), eicosapentaenoic acid (EPA, 20:5 n3) and arachidonic acid (ARA, 20:4 n6).

11. A method for improving intestinal barrier integrity in an infant or toddler by administering a nutritional composition selected from an infant formula or a follow-up formula and which is not human milk, that comprises a 2'-fucosyllactose.

12. The method according to claim 11, wherein the improvement of intestinal barrier integrity is a reduction in the permeability of the intestinal barrier.

13. The method according to claim 11, wherein the nutritional composition further comprises at least one non-digestible oligosaccharides with a DP in the range of 2 to 250, wherein the non-digestible oligosaccharides are selected from the group consisting of fructo-oligosaccharides, galacto-oligosaccharides, xylo-oligosaccharides, arabino-oligosaccharides, arabinogalacto-oligosaccharides, gluco-oligosaccharides, chito-oligosaccharides, glucomanno-oligosaccharides, galactomanno-oligosaccharides and mannan-oligosaccharides.

14. The method according to claim 13, wherein the non-digestible oligosaccharides are selected from the group consisting of fructo-oligosaccharides and galacto-oligosaccharides.

15. The method according to claim 11, wherein the nutritional composition further comprises at least one long chain polyunsaturated fatty acids (LC-PUFA) selected from the group consisting of eicosapentaenoic acid (EPA, 20:5 n3), docosahexaenoic acid (DHA, 22:6 n3), arachidonic acid (ARA, 20:4 n6) and docosapentaenoic acid (DPA, 22:5 n3).

16. The method according to claim 11, wherein the human subject is an infant.

17. The method according to claim 11, wherein the nutritional composition is an infant formula.

* * * * *